United States Patent
Foo (12)

(10) Patent No.: US 6,393,313 B1
(45) Date of Patent: May 21, 2002

(54) PRODUCING A PHASE CONTRAST MR IMAGE FROM A PARTIAL FOURIER DATA ACQUISITION

(75) Inventor: Thomas K. F. Foo, Rockville, MD (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 0 days.

(21) Appl. No.: 09/644,444

(22) Filed: Aug. 23, 2000

(51) Int. Cl.[7] .............................................. A61B 5/055
(52) U.S. Cl. ........................ 600/410; 324/307; 324/309
(58) Field of Search ................................ 600/410, 420, 600/425, 419; 324/306, 309, 307

(56) References Cited

U.S. PATENT DOCUMENTS

| 5,093,620 A | | 3/1992 | Pelc et al. ................... 324/306 |
| 5,168,227 A | | 12/1992 | Foo et al. ................... 324/309 |
| 5,923,789 A | * | 7/1999 | Avinash ...................... 382/276 |
| 6,167,293 A | * | 12/2000 | Chenevert et al. .......... 600/420 |
| 6,185,447 B1 | * | 2/2001 | Alley et al. ................. 600/420 |
| 6,198,283 B1 | * | 3/2001 | Foo et al. ................... 324/309 |
| 6,198,959 B1 | * | 3/2001 | Wang .......................... 600/413 |
| 6,208,139 B1 | * | 3/2001 | Foo et al. ................... 324/309 |
| 6,230,040 B1 | * | 5/2001 | Wang et al. ................. 600/415 |

OTHER PUBLICATIONS

Homodyne Detection in Magnetic Resonance Imaging, IEEE Trans. Med. Imaging 1991; 10:154–63, D.C. Noll, et al.

* cited by examiner

Primary Examiner—Marvin M. Lateef
Assistant Examiner—Eleni Mantis Mercader
(74) Attorney, Agent, or Firm—Quarles & Brady, LLP; Christian G. Cabou

(57) ABSTRACT

A cardiac triggered, fast gradient-recalled echo pulse sequence is used to acquire a partial Fourier image data set during a single breath-hold. The image data is velocity encoded and a velocity image is produced by zero-filling and Fourier transforming the zero-filled data set. A separate magnitude image is produced by performing a homodyne reconstruction on the partial Fourier image data set. Anatomic information, such as artery size, is obtained from the magnitude image and combined with velocity information from the velocity image to measure blood flowing through an artery.

18 Claims, 4 Drawing Sheets

PRODUCING A PHASE CONTRAST MR IMAGE FROM A PARTIAL FOURIER DATA ACQUISITION

BACKGROUND OF THE INVENTION

The field of the invention is nuclear magnetic resonance imaging ("MRI") methods and systems. More particularly, the invention relates to the acquisition of partial velocity encoded MRI data sets and the reconstruction of images from such data sets.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, $M_z$, may be rotated, or "tipped", into the x-y plane to produce a net transverse magnetic moment $M_t$. A signal is emitted by the excited spins after the excitation signal $B_1$ is terminated, this signal may be received and processed to form an image.

When utilizing these signals to produce images, magnetic field gradients ($G_x$, $G_y$ and $G_z$) are employed. Typically, the region to be imaged is scanned by a sequence of measurement cycles in which these gradients vary according to the particular localization method being used. The resulting set of received NMR signals are digitized and processed to reconstruct the image using one of many well-known reconstruction techniques.

The present invention will be described in detail with reference to a variant of the well-known Fourier transform (FT) imaging technique, which is frequently referred to as "spin-warp". The spin-warp technique is discussed in an article entitled "Spin-Warp NMR Imaging and Applications to Human Whole-Body Imaging" by W. A. Edelstein et al., *Physics in Medicine and Biology*, Vol. 25, pp. 751–756 (1980). It employs a variable amplitude phase encoding magnetic field gradient pulse prior to the acquisition of NMR spin-echo signals to phase encode spatial information in the direction of this gradient. In a two-dimensional implementation (2DFT), for example, spatial information is encoded in one direction by applying a phase encoding gradient ($G_y$) along that direction, and then a spin-echo signal is acquired in the presence of a readout magnetic field gradient ($G_x$) in a direction orthogonal to the phase encoding direction. The readout gradient present during the spin-echo acquisition encodes spatial information in the orthogonal direction. In a typical 2DFT pulse sequence, the magnitude of the phase encoding gradient pulse $G_y$ is incremented ($\Delta G_y$) in the sequence of views that are acquired during the scan to sample so-called "k-space" and thereby produce a set of NMR data from which an image can be reconstructed. The phase encoding gradient $G_y$ steps from a negative value through zero to a corresponding positive value to sample k-space symmetrically around its origin.

Most NMR scans currently used to produce medical images require many minutes to acquire the necessary data. The reduction of this scan time is an important consideration, since reduced scan time increases patient throughput, improves patient comfort, and improves image quality by reducing motion artifacts. The reduction of scan time in ECG gated cardiac imaging is particularly important in order to acquire the image data within a single patient breath-hold. This avoids respiratory gating and the introduction of image artifacts caused by respiratory motion.

One method for reducing scan time is to reduce the total number of views acquired during the scan. Instead of sampling k-space symmetrically around the origin, only spatial frequencies on one side of the origin plus a small amount near the origin on the opposite side are sampled. For example, instead of stepping $G_y$ through 128 values ranging from −64 to +64, only the views ranging from −64 to +8 are acquired. As a result, fewer views are acquired which shortens scan time, but some k-space data is missing from the acquired data set.

Another method for reducing scan time is to acquire a partial NMR echo signal as described in U.S. Pat. No. 5,168,227. This moves the time to the echo signal peak (TE) closer to the start of the readout gradient waveform, shortens the readout gradient waveform, and shortens the transmit repeat time (TR) of the pulse sequence. For example, the TR of a gradient recalled echo pulse sequence can be shortened from 7–8 msec. to 2–6 msec. with a resulting 20% reduction in scan time to acquire an image. However, k-space along the readout gradient axis is not fully sampled when a partial echo is acquired and some k-space data is missing in the resulting k-space image data set.

There are two basic methods used to reconstruct images from such "partial" Fourier image data sets. The first method is referred to in the art as "zero filling". As the name suggests, the missing k-space data is set to zero and a normal Fourier transformation of the zero-filled k-space image data set is performed to reconstruct an image. Unfortunately, the magnitude image produced with a zero-filled k-space data set has reduced resolution, or spatial blurring.

A second method for reconstructing an image from a partial Fourier image data set uses Hermitian conjugate symmetry to replace the missing k-space data. Hermitian conjugate symmetry only works if the image is real. Numerous phase errors are present in MRI data that make the image complex. These phase errors result from phenomena such as $B_0$ inhomogeneity, gradient eddy currents, group delays in the gradient amplifiers and receive electronics, and the spatial variation of surface coil receive B1 fields. To enable Hermitian conjugate replacement to work with a complex image, the replacement of the missing k-space data is accompanied by a phase correction which removes the phase errors from this data. One partial Fourier reconstruction algorithm, called "Homodyne reconstruction", uses two filters to accomplish the Hermitian conjugate replacement and the phase correction, respectively, Noll D C, Nishimura O G, and Macovski A, "Homodyne Detection in Magnetic Resonance Imaging," *IEEE Trans. Med. Imaging* 991; 10:154–63. A Homodyne high pass filter doubles the amplitude of the acquired k-space data which is conjugate to the missing k-space data prior to the Fourier transform. After the Fourier transform and phase correction, the imaginary part of the image is discarded to complete the replacement step. The phase correction step is accomplished by a Homodyne low pass filter. This filter creates an image from a small portion of k-space data acquired symmetrically around the center of k-space. The phase of this image is subtracted from the phase of the Homodyne high pass filtered image prior to discarding the imaginary part of the image.

Although some phase information may be preserved when performing the Homodyne reconstruction, it has been found that phase images produced with this method have increased spatial blurring.

MR images which indicate the velocity of moving spins may be acquired by employing a velocity encoding gradient in the pulse sequence as described in U.S. Pat. No. 5,093, 620. Such images indicate blood flow velocity in images and they are useful to provide quantitative measurements of blood flow volume through arteries. To reconstruct a velocity image, however, the phase information in the acquired k-space image data set must be accurately preserved. As a result, MR velocity imaging has necessitated the acquisition of the entire Fourier image data set.

SUMMARY OF THE INVENTION

The present invention is a method and apparatus for reconstructing both magnitude and phase images from partial Fourier MR image data sets. More specifically, a complex partial k-space image data set is acquired using a pulse sequence which employs a velocity encoding gradient, a first complex image is reconstructed from the complex partial k-space image data set using a homodyne reconstruction process, a magnitude image is constructed from the real part of the first complex image, the complex partial k-space image data set is zero-filled, a second complex image is reconstructed from the zero-filled complex k-space image data set, and a velocity image is constructed from phase information in the second complex image. The magnitude image may be used to obtain an accurate measurement of an artery or other structure through which blood is flowing and the velocity image may be used to measure the average velocity. From these measurements, blood flow volume may be computed.

The present invention has particular application where blood flow through an artery, heart valve, or other structure is to be measured and motion due to patient respiration is an issue. A partial Fourier acquisition may be employed to shorten scan time and enable the data to be acquired in a single breath-hold. Accurate anatomic information is produced by the magnitude image and accurate velocity information is produced from the velocity image. An accurate depiction of the vessel boundaries is important as the flow (i.e., velocity times cross-sectional area) is highly dependent on the correct measure of the anatomic cross-sectional area of the vessel.

GENERAL DESCRIPTION OF THE INVENTION

Figure 1:
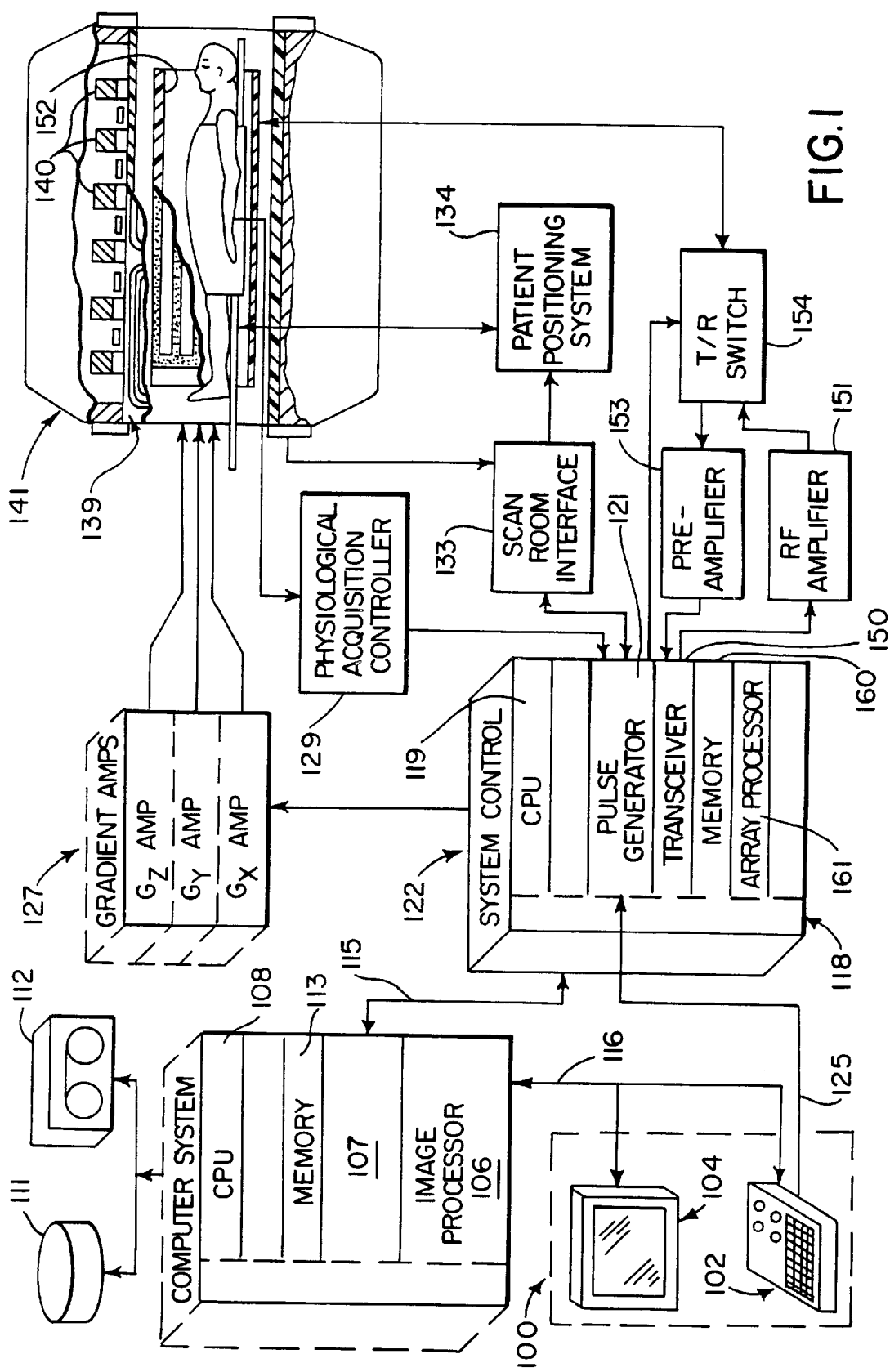
FIG. 1 is a block diagram of an MRI system which employs the present invention.

In MR imaging, one can reduce the echo time by using a fractional echo (partial Fourier acquisition in the frequency direction) or reduce scan time by using fractional excitation or NEX (partial Fourier in the phase encoding direction). However, in partial echo or partial-Fourier reconstruction strategies that use Hermitian symmetry, such as the homodyne reconstruction method, all phase information is lost.

Partial Fourier data can also be reconstructed using zero-filling. The zero-filled interpolated image (in one-dimension) is $$I_Z(x) = f_L(x)e^{j\phi_L(x)} + \frac{1}{2}f_H(x)e^{j\phi_H(x)} * \left(\delta(x) + \frac{1}{j\pi x}\right) \quad (1)$$

which is equivalent to multiplying a full k-space data set by $W_N(k)$, where $$W_N(k) = \begin{cases} 0, & k < -k_0 \\ 1, & \text{otherwise} \end{cases} \quad (2)$$

and Fourier transforming the result. Note that $f_L(x)$ and $f_H(x)$ represent the real-valued images reconstructed from low and high spatial frequency components, respectively. Similarly, $\phi_L(x)$ and $\phi_H(x)$ represent the corresponding phase contributions from the low and high spatial frequency components.

An alternative to simple zero-filling is to weight the high spatial frequencies by a factor of two before reconstructing the zero-filled data set as $$I_C(x) = f_L(x)e^{j\phi_L(x)} + f_H(x)e^{j\phi_H(x)} * \left(\delta(x) + \frac{1}{j\pi x}\right), \quad (3)$$

which is equivalent to the Fourier transform of the MR data after applying a filter, $W_{HH}$, to the k-space data, where $$W_{HH}(k) = \begin{cases} 0, & k < -k_0 \\ 1, & -k_0 \leq k \leq +k_0 \\ 2, & k > +k_0 \end{cases} \quad (4)$$

A third method for reconstruction attempts to compensate for the error term in Eq. 3 and is based on the homodyne reconstruction technique of Noll, et al. "Homodyne Detection In Magnetic Resonance Imaging", *IEEEE Trans. Med. Imaging* 1991; 10:154–163. If we assume that the phase in the image is slowly varying, $\exp(j\phi_H(x)) \approx \exp(j\phi_L(x))$ and $$\exp(j\phi_L(x)) = \frac{g_L(x)}{\|g_L(x)\|} \quad (5)$$

where $g_L(x)$ is the complex-valued Fourier transform of the low-pass filtered k-space data from $[-k_0, \ldots, +k_0]$ (after applying $W_L(k)$ to the k-space data), where $$W_L(k) = \begin{cases} 0, & -k_0 < k < +k_0 \\ 1, & \text{otherwise} \end{cases} \quad (6)$$

the phase term from the high spatial frequencies in Eq. 3 can be extracted to yield $$\tilde{I}_C(x) \approx f_L(x)e^{j\phi_L(x)} + f_H(x)e^{j\phi_L(x)} - j\left(f_H(x) * \frac{1}{\pi x}\right)e^{j\phi_L(x)} \quad (7)$$

The convolution term represents the error term from having only partial k-space data. If this error term can be determined and subtracted from Eq. 7, the complex-valued image will provide phase and magnitude information. Similarly, Eq. 1 can be simplified to $$\tilde{I}_Z(x) \approx \left(f_L(x) + \frac{1}{2}f_H(x) - \frac{j}{2}f_H(x) * \frac{1}{\pi x}\right)e^{j\phi_L(x)} \quad (8)$$

$$-\left(f_H(x) * \frac{1}{\pi x}\right) \approx 2 \cdot \text{Imag}[\tilde{I}_Z(x)e^{-j\phi_L(x)}] \quad (9)$$

The error term from Eq. 9 can be used to eliminate the corresponding error term from $\tilde{I}_c$, while retaining magnitude and phase information $$I_R(x) = \tilde{I}_c(x) - 2 \cdot j\text{Imag}[\tilde{I}_z(x)e^{-j\phi_L(x)}]e^{j\phi_L(x)} \quad (10)$$

$$\approx f_L(x)e^{j\phi_L(x)} + f_H(x)e^{j\phi_H(x)} - \epsilon(x) \quad (11)$$

where $\epsilon(x)$ represents an error term from the approximation that the phase is slowly varying and that $\phi_H(x) \approx \phi_L(x)$.

The root mean squared (r.m.s.) error from all three partial k-space phase contrast reconstruction approaches are listed in Table 1. The root mean squared (r.m.s.) error of velocity measurements (in cm/s) of the three different methods of reconstructing partial k-space phase contrast data in the femoral artery and in the descending aorta are measured across all cardiac phases. The number of phase encoding ($k_y$ lines) actually acquired and the number of $k_y$ lines used in the partial Fourier reconstructions are listed along with the corresponding r.m.s. error from a full Fourier acquisition and measurement. It is clear that simple zero-filling has the least error of all three techniques. Moreover, simple zero-filling can be used with partial k-space in the phase encoding and partial echo (in the read-out) direction with a small increase in the r.m.s. error in the phase velocity measurements.

TABLE 1

| | | | | r.m.s. Error in Velocity (cm/s) | | |
|---|---|---|---|---|---|---|
| | acq. $k_y$ lines | frac. $k_y$ lines | VENC (cm/s) | phase h-dyne | wgt. zero-fill | Zero-fill |
| Subject A | | | | | | |
| Femoral art. | 204 | 134 | 120 | 1.27 | 0.55 | 0.60 |
| Femoral art. | 204 | 156 | 120 | 0.43 | 0.32 | 0.17 |
| Aorta | 256 | 160 | 120 | 0.26 | 0.21 | 0.10 |
| Aorta | 256 | 192 | 120 | 0.10 | 0.05 | 0.06 |
| Subject B | | | | | | |
| Aorta | 128 | 80 | 80 | 1.48 | 0.91 | 0.62 |
| Aorta | 128 | 96 | 80 | 0.67 | 0.56 | 0.48 |
| Aorta | 128 | 80 | 120 | 0.47 | 0.96 | 0.51 |
| Aorta | 128 | 96 | 120 | 0.36 | 0.30 | 0.22 |
| Subject C | | | | | | |
| Aorta | 256 | 160 | 120 | 0.61 | 0.58 | 0.18 |
| Aorta | 256 | 192 | 120 | 0.19 | 0.14 | 0.07 |

When phase velocity images are examined, the phase image using phase sensitive homodyne reconstruction exhibits a severe loss in spatial resolution along the partial Fourier direction. The zero-filled phase image shows much improved spatial resolution although it is still not comparable to a full k-space phase velocity image. Weighted zero-filling produces phase velocity images comparable to simple zero-filling but with increased noise.

However, when magnitude images are examined, the converse is true. Simple zero-filling and weighted zero-filling both produce magnitude images with increased spatial blurring compared to conventional homodyne reconstruction. The magnitude images from a conventional homodyne reconstruction yields images that are comparable to full k-space magnitude images.

The reasons for these observations may be found in Eqs. 1–11. With zero-filling (Eq. 1), the magnitude image will have considerable blurring due to the absence of one-half of the high spatial frequency k-space data. Although the magnitude of $f_H(x)$ is reduced by ½, the phase information, $\phi_H(x)$, is unaffected by the ½ scaling and retains the high spatial frequency component information. However, the additional loss in spatial resolution in the phase image is due to the error from the convolution of the phase term with $1/\pi x$ (in Eq. 1). Hence, the spatial resolution degradation in phase image is not as severe as that in the magnitude image.

In the phase sensitive homodyne reconstruction of Eq. 10, high spatial frequency information is recovered in the magnitude image but the phase image is blurred from the imposition of the $e^{j\phi_L(x)}$ term applied in Eq. 10. Since this correction assumes that the low spatial frequency phase can be applied to the entire image, it is unreasonable to expect that the phase component will be dominated by $e^{j\phi_L(x)}$. This then leads to the errors in the phase-velocity measurements.

As in any partial Fourier technique, the extent of the k-space information is inversely proportional to vessel size, i.e., the smaller the vessel, the larger the k-space extent of the information needed to reconstruct an image of the vessel with minimal loss of fidelity. In the present invention there is no significant difference in the measured r.m.s. error in a small vessel such as the femoral artery as compared to the aorta.

DESCRIPTION OF THE PREFERRED EMBODIMENT

Referring first to FIG. 1, there is shown the major components of a preferred MRI system which incorporates the present invention. The operation of the system is controlled from an operator console 100 which includes a keyboard and control panel 102 and a display 104. The console 100 communicates through a link 116 with a separate computer system 107 that enables an operator to control the production and display of images on the screen 104. The computer system 107 includes a number of modules which communicate with each other through a backplane. These include an image processor module 106, a CPU module 108 and a memory module 113, known in the art as a frame buffer for storing image data arrays. The computer system 107 is linked to a disk storage 111 and a tape drive 112 for storage of image data and programs, and it communicates with a separate system control 122 through a high speed serial link 115.

The system control 122 includes a set of modules connected together by a backplane. These include a CPU module 119 and a pulse generator module 121 which connects to the operator console 100 through a serial link 125. It is through this link 125 that the system control 122 receives commands from the operator which indicate the scan sequence that is to be performed. The pulse generator module 121 operates the system components to carry out the desired scan sequence. It produces data which indicates the timing, strength and shape of the RF pulses which are to be produced, and the timing of and length of the data acquisition window. The pulse generator module 121 connects to a set of gradient amplifiers 127, to indicate the timing and shape of the gradient pulses to be produced during the scan. The pulse generator module 121 also receives patient data from a physiological acquisition controller 129 that receives signals from a number of different sensors connected to the patient, such as ECG signals from electrodes or respiratory signals from a bellows. And finally, the pulse generator module 121 connects to a scan room interface circuit 133 which receives signals from various sensors associated with the condition of the patient and the magnet system. It is also through the scan room interface circuit 133 that a patient positioning system 134 receives commands to move the patient to the desired position for the scan.

The gradient waveforms produced by the pulse generator module 121 are applied to a gradient amplifier system 127 comprised of $G_x$, $G_y$ and $G_z$ amplifiers. Each gradient amplifier excites a corresponding gradient coil in an assembly generally designated 139 to produce the magnetic field gradients used for position encoding acquired signals. The gradient coil assembly 139 forms part of a magnet assembly 141 which includes a polarizing magnet 140 and a whole-body RF coil 152. A transceiver module 150 in the system control 122 produces pulses which are amplified by an RF amplifier 151 and coupled to the RF coil 152 by a transmit/receive switch 154. The resulting signals radiated by the excited nuclei in the patient may be sensed by the same RF coil 152 and coupled through the transmit/receive switch 154 to a preamplifier 153. The amplified NMR signals are demodulated, filtered, and digitized in the receiver section of the transceiver 150. The transmit/receive switch 154 is controlled by a signal from the pulse generator module 121 to electrically connect the RF amplifier 151 to the coil 152 during the transmit mode and to connect the preamplifier 153 during the receive mode. The transmit/receive switch 154 also enables a separate RF coil (for example, a head coil or surface coil) to be used in either the transmit or receive mode.

The NMR signals picked up by the RF coil 152 are digitized by the transceiver module 150 and transferred to a memory module 160 in the system control 122. When the scan is completed and an entire array of data has been acquired in the memory module 160, an array processor 161 operates to Fourier transform the data into an array of image data. This image data is conveyed through the serial link 115 to the computer system 107 where it is stored in the disk memory 111. In response to commands received from the operator console 100, this image data may be archived on the tape drive 112, or it may be further processed by the image processor 106 and conveyed to the operator console 100 and presented on the display 104. For a more detailed description of the transceiver 150, reference is made to U.S. pat. Nos. 4,952,877 and 4,992,736 which are incorporated herein by reference.

Figure 2:
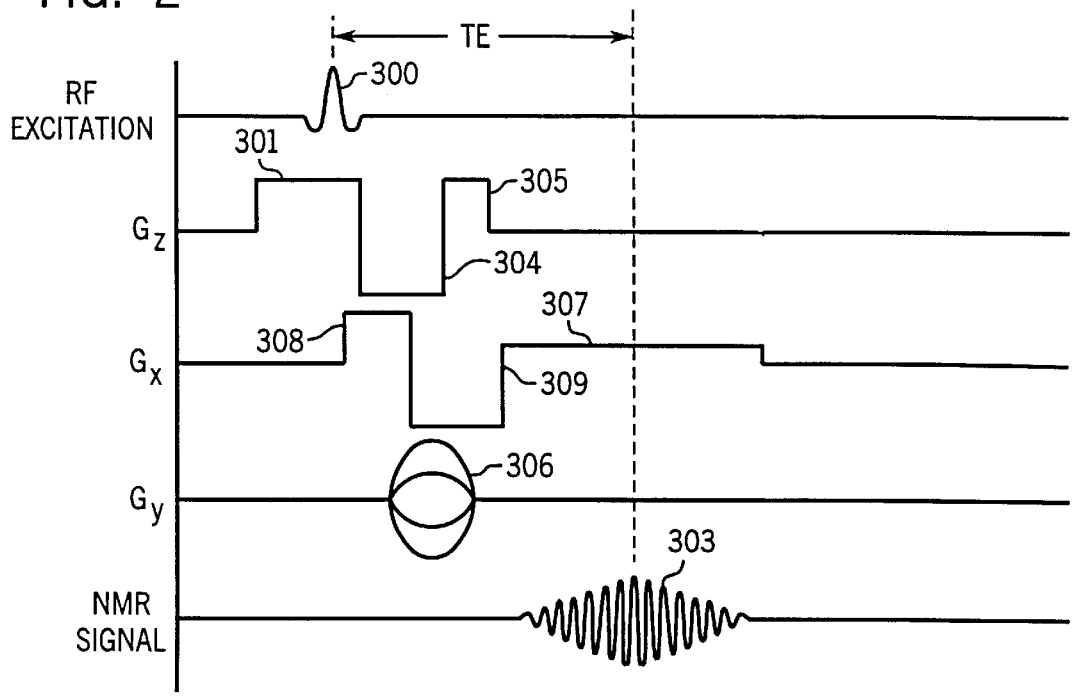
FIG. 2 is an exemplary pulse sequence that may be employed by the MRI system of FIG. 1 to acquire MR image data.

The NMR system of FIG. 1 performs a series of pulse sequences to collect sufficient NMR data to reconstruct the desired velocity image. Referring particularly to FIG. 2, the preferred pulse sequence employs a selective RF excitation pulse 300 which is applied to the subject in the presence of a $G_z$ slice select gradient pulse 301. The excitation pulse 300 has a flip angle of α. To compensate the NMR signal 303 which is produced at a time TE after the excitation pulse 300 for the phase shifts caused by the slice select gradient pulse 301 and to desensitize the NMR signal 303 to velocity along the z-axis, a negative $G_z$ gradient pulse 304 followed by a positive $G_z$ gradient pulse 305 are produced by the $G_z$ gradient coils as taught in U.S. Pat. No. 4,731,583. For example, one solution is to use a pulse 304 of the same width but opposite sign as the pulse 301 and the pulse 305 is one half the width and the same height as pulse 301. While the pulses 304 and 305 compensate for velocity along the z-axis, more complex gradient waveforms are also well known to those skilled in the art for compensating acceleration and even higher orders of motion.

To position encode the NMR signal 303 a phase encoding $G_y$ gradient pulse 306 is applied to the subject shortly after the application of the RF excitation pulse 300. As is well known in the art, a complete scan is comprised of a series of these pulse sequences in which the value of the $G_y$ phase encoding pulse is stepped through a series of, for example, 128 or 256 discrete phase encoding values to localize the position of the spins producing the NMR signal along the y-axis. Position along the x-axis is located by a $G_x$ gradient pulse 307 which is produced as the NMR gradient echo signal 303 is acquired and which frequency encodes the NMR signal 303. Unlike the $G_y$ phase encoding gradient pulse 306, the $G_x$ readout gradient pulse 307 remains at a constant value during the entire scan. To produce the gradient echo 303 and to desensitize it to velocity along the x direction, gradient pulses 308 and 309 precede the gradient pulse 307 as taught in U.S. Pat. No. 4,731,583.

The NMR signal 303 is acquired by the system transceiver 122 and digitized into a row of 256 complex numbers which are stored in the memory of the main computer 101. For each value of the $G_y$ phase encoding gradient an NMR signal 303 is produced, acquired, digitized and stored in a separate row of 256 complex numbers. At the completion of the scan, therefore, a two-dimensional matrix of complex numbers is stored in the computer 101. These NMR signals which are produced when no flow sensitizing gradients are applied may be Fourier transformed into a conventional NMR image. The image data produced from these flow compensated signals is referred to herein as the reference image data.

Additional measurement cycles are conducted to acquire the velocity encoded data needed to practice the present invention. These measurement cycles employ the pulse sequence of FIG. 2 with one important difference—they include motion encoding magnetic field gradients which sensitize the NMR signal 303 to velocity along one axis. These motion encoding field gradients are produced by the same coils that produce the position encoding gradients $G_x$, $G_y$ and $G_z$ in the pulse sequence of FIG. 2. For a simple case in which velocity encoding along the x, y or z axis is desired, a bipolar gradient directed along that axis is added to the pulse sequence of FIG. 2. In the more general case where the velocity encoding direction is oriented at an oblique angle, the motion encoding measurements are made by applying a combination of bipolar gradients as will now be described with reference to FIG. 3.

Figure 3:
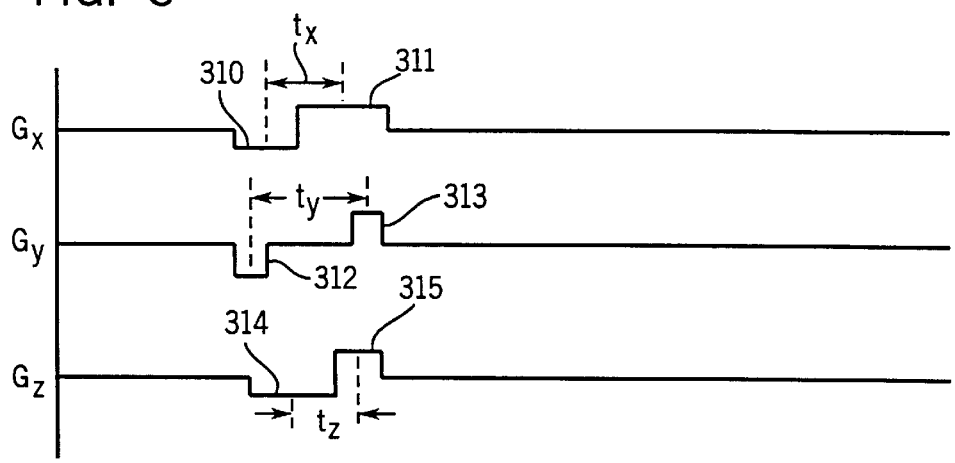
FIG. 3 is a graphic representation of velocity encoding gradients added to the pulse sequence of FIG. 2.

A velocity encoding measurement may be made with the additional gradient pulses 310–315 shown in FIG. 3. These additional gradient pulses 310–315 are added to the motion compensated gradient pulses of FIG. 2 and they produce bipolar gradients along the respective x, y and z axes. These bipolar gradient pulses 310/311, 312/313, and 314/315 sensitize the subsequent NMR signal 303 to the velocity of spins moving along the x, y and z axes. The area, $A_x$, of each pulse 310 and 311 is the same and they are spaced apart by a time $t_x$. The change in the first moment is, therefore, $\Delta Mx_1 = A_x t_x$. Similarly, pulses 312 and 313 each having an area $A_y$, are spaced apart by time $t_y$, and produce a first moment change $\Delta Mx_1 = A_y t_y$. Pulses 314 and 315 have equal areas $A_z$ and are spaced apart by a time $t_z$. They produce a change in first moment $\Delta Az_1 = A_z t_z$. These first moment changes $\Delta Mx_1$, $\Delta My_1$ and $\Delta Az_1$ determine the velocity sensitivity, which is typically controlled by adjusting the areas $A_x$, $A_y$ and $A_z$ respectively.

It should be apparent to those skilled in the art that many other pulse sequences can be used to acquire the necessary data. Also, there are many different ways to produce the motion encoding gradients for each measurement. For example, the gradient pulses can be shaped differently than those shown in FIG. 3, or they may be more separated in time to increase the first moment, or they may be more compact in their temporal duration. Also, spin echo sequences using a 180° RF pulse may be used, and rather than using bipolar gradient pulses, both velocity encoded pulses may have the same polarity if they are produced on opposite sides of the 180° RF pulse.

Figure 4:
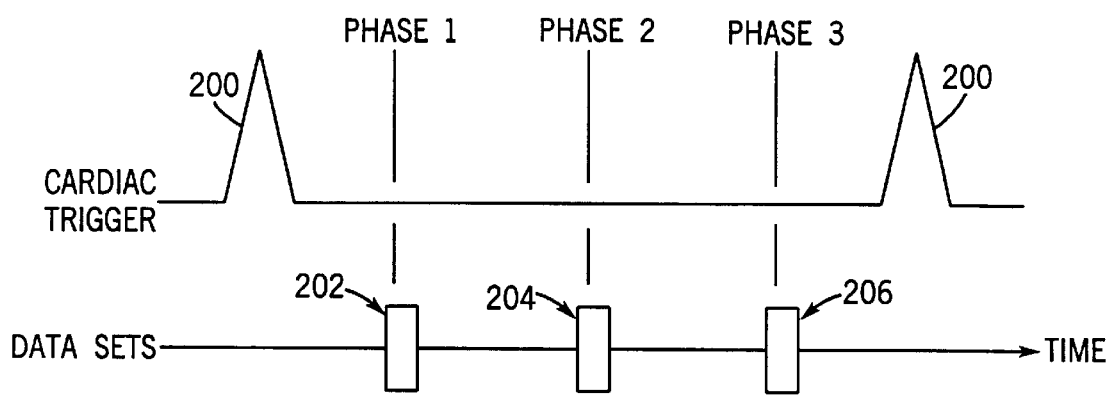
FIG. 4 is a graphic representation of an ECG triggered acquisition using the pulse sequence of FIG. 2.

Referring particularly to FIG. 4, an ECG gated acquisition employs a series of fast gradient echo pulse sequences, such as those in FIG. 2. These pulse sequences are executed during the interval between the cardiac trigger signals 200 referred to as the R—R interval. The length of the R—R interval is a function of the patient's heart rate. The R—R interval is divided up into many short segments, with each segment being n fast gradient acquisition pulse sequence. Each fast gradient echo pulse sequence acquires an NMR signal representing a single line of k-space which is sometimes referred to as a phase encoded view, or a view. "n" is often referred to as the number of phase encoded views per segment and is typically from 1 to 8. The data from each segment contributes to generating an image at different temporal phases of the cardiac cycle (R—R interval). The temporal location of these phase images depends on the relative time from the cardiac trigger (R-wave) 200 to the center of each segment. In FIG. 4, the first segment acquires views for a first k-space data set 202. The next echo segment acquires views at a second cardiac phase for a second k-space data set 204, and a third segment acquires views for a third k-space data set 206.

If a segment includes n=4 views, two acquisitions are acquired with opposite velocity encoding gradients, and a complete 256×256 k-space image data set is acquired for image data sets 202, 204 and 206, the scan will require a minimum of 256/(2×4)=32 heart beats. This requires that the patient hold their breath for approximately 30 seconds. On the other hand, by using the present invention in which partial k-space data sets are acquired, the scan requires approximately 20 seconds (192/8=24 heartbeats). This is a significant reduction in scan time and enables a comfortable breath-holding period even for an infirm patient.

Figure 5:
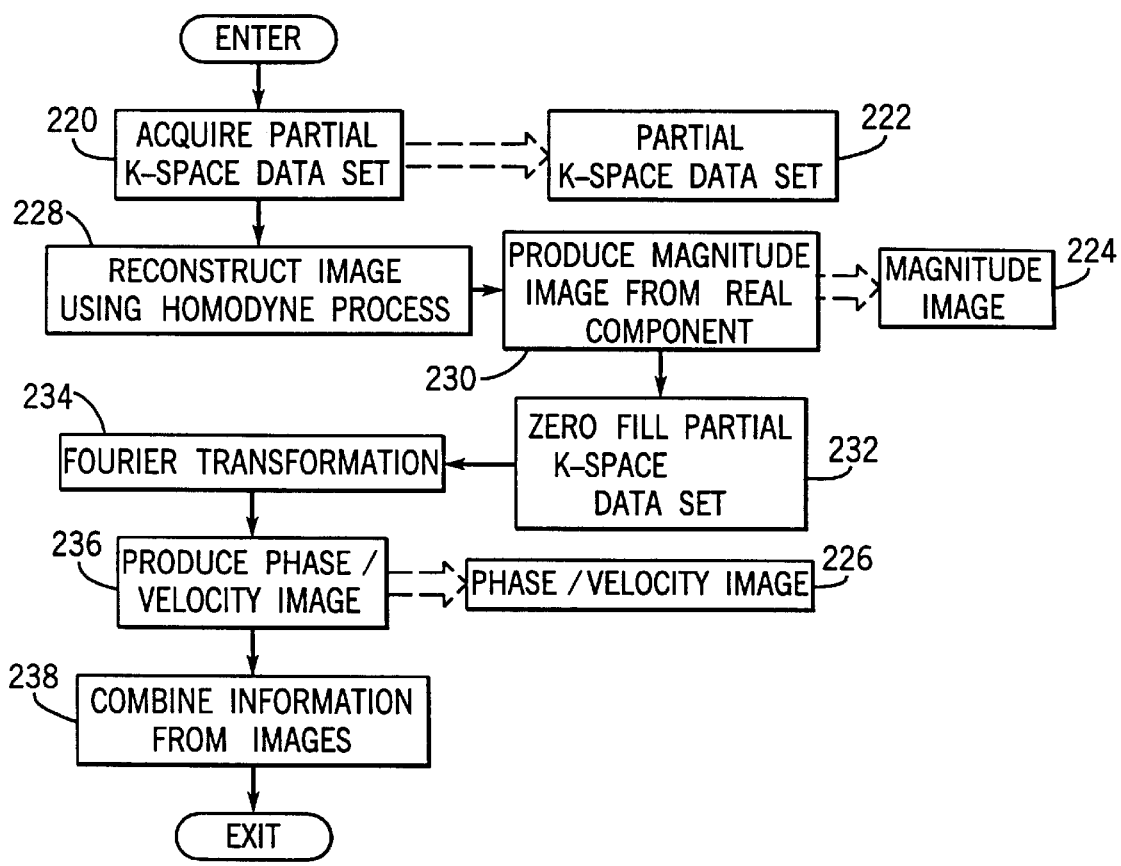
FIG. 5 is a flow chart of the steps used to process the partial Fourier image data set according to a preferred embodiment of the invention.

Referring particularly to FIG. 5, a scan is performed on a subject positioned in the MRI system using the pulse sequence of FIG. 2. As indicated at process block 220, a partial k-space data set 222 is acquired by repeating the pulse sequence over a series of heart beats as described above. In the preferred embodiment, for example, only 0.625 times the number of views for a complete k-space data set (i.e. 0.625×128=80 or 0.625×256=160) are acquired during the scan. It can be appreciated by those skilled in the art that other information may also be acquired during the scan, such as reference image data that may be subtracted from the final phase/velocity image to remove system phase errors.

The acquired partial k-space image data set 222 is processed separately to produce a magnitude image 224 and a phase/velocity image 226. More specifically, an image is reconstructed as indicated at process block 228 using a standard homodyne reconstruction as discussed above. No measures are taken to preserve accurate phase information during this reconstruction, since as indicated at process block 230, the magnitude image 224 is produced from only the real part of the homodyne reconstructed image. The resolution of this magnitude image 224 has been found to be clinically equivalent to a magnitude image reconstructed from a complete k-space image data set.

A phase/velocity image 226 is also reconstructed from the partial k-space image data set 222. As indicated at process block 232, the first step is to zero-fill the array which stores the acquired k-space image data 222. It can be appreciated that this step may be performed before the scan is performed by initializing the data array into which the acquired k-space data 222 is stored. As indicated at process block 234, a conventional Fourier transformation is then performed to produce a complex image. Each complex image element is comprised of quadrature components I and Q, and a phase image is calculated at process block 236 where each element in the phase image is:

$$\phi=\tan^{-1}(I/Q).$$

This phase image may be converted to provide a quantitative indication of spin velocity by multiplying each phase element $\phi_{xy}$ by a value determined by the first moment of the velocity encoding gradient used in the pulse sequence of FIG. 2.

$$V_{xy}=\phi_{xy}/\gamma\Delta M_1$$

where $=\Delta M_1=\pi/\gamma$VENC—first moment of the flow encoding gradients;

VENC=the maximum flow encoding value.

The accuracy of the phase/velocity indications in this image 226 have been found to be clinically equivalent to a phase/velocity image reconstructed from a complete k-space image data set.

As indicated at process block 238, the structural, anatomic information in the magnitude image 224 may be combined with the velocity information in the phase/velocity image 226 to measure flow through a region of interest such as an artery. The exact cross sectional area of an artery, for example, can be determined from the magnitude image 224, and the average velocity of blood flowing through that artery can be determined from the phase/velocity image 226. Multiplying the two measurements provides the blood flow volume through the artery.

An alternative method for quantitatively measuring flow through a region of interest such as an artery is to identify each pixel located in the artery using the magnitude image 224. The flow indicated by each corresponding pixel in the phase/velocity image 226 is summed to provide a total flow through the artery.

It should be apparent that many variations are possible from the preferred embodiment described above without departing from the invention. Other motion encoding pulse sequences may be employed and additional partial k-space image data sets may be acquired to measure velocity along two or three axes. The present invention is particularly applicable to imaging regions which are subject to respiratory motion and in which the acquisition is to be performed during a patient breath-hold, but many other applications are possible where a reduction in scan time without a loss in anatomic resolution or phase measurement accuracy is desired.

What is claimed is:

1. A method for producing an image of a subject with a magnetic resonance imaging (MRI) system, the steps comprising:

a) acquiring a partial k-space image data set with the MRI system using a pulse sequence that employs a motion encoding gradient;

b) reconstructing a first image from the partial k-space image data set using a homodyne reconstruction process;

c) producing a magnitude image from a real component of the first image;

d) reconstructing a second, complex valued image by zero-filling the partial k-space image data set and performing a complex Fourier transformation thereon; and e) producing a phase image from the second complex image using the phase information therein.

2. The method as recited in claim 1 which includes:

f) combining information in the magnitude image with information the phase image.

3. The method as recited in claim 1 which includes producing a velocity image from the phase image.

4. The method as recited in claim 3 which includes:

f) combining information in the magnitude image with information in the velocity image.

5. The method as recited in claim 1 in which the motion encoding gradient is a bipolar gradient that encodes for motion.

6. The method as recited in claim 5 which includes producing a velocity image from the phase image.

7. The method as recited in claim 6 which includes:

f) combining anatomic information in the magnitude image with velocity information in the velocity image.

8. The method as recited in claim 7 in which the anatomic information is the size of an artery in the subject and step f) determines the amount of blood flowing through the artery.

9. The method as recited in claim 1 in which k-space is completely sampled by a preset number of views, and the partial k-space image data set is comprised of a set of views which sample less than all regions of k-space.

10. The method as recited in claim 1 which includes:

receiving a signal indicative of the subject's heart beat; and synchronizing the acquisition of the partial k-space image data set with the subject's heart beat.

11. The method as recited in claim 10 which includes:

producing a velocity image from the phase image; and combining information in the magnitude image with information in the velocity image.

12. The method as recited in claim 11 in which the information in the magnitude image is the size of an artery in the subject and the information in the velocity image is the velocity of blood flow through the artery.

13. A magnetic resonance imaging (MRI) system which comprises:

a magnet for producing a polarizing magnetic field;

an rf system for exciting spins in a subject positioned in the polarizing field and for receiving an NMR signal produced by excited spins;

a gradient system for producing magnetic field gradients in the subject;

a pulse generator connected to operate the rf system and the gradient system and being operable to perform a series of pulse sequences in which a velocity encoded, partial k-space image data set is acquired;

means for performing a homodyne image reconstruction to produce a first image from the partial k-space image data set;

means for producing a magnitude image from the first image;

means for performing a zero-filled Fourier transformation of the partial k-space data set to produce a second complex image;

means for producing a phase image from the second complex image; and means for combining information in the magnitude image with information in the phase image.

14. The MRI system as recited in claim 13 which includes means responsive to a signal indicative of the patient's heart beat for synchronizing the operation of the pulse generator therewith.

15. The MRI system as recited in claim 14 which includes means for calculating a velocity image from the phase image.

16. The MRI system as recited in claim 15 in which velocity information in the velocity image is combined with anatomic information in the magnitude image to determine the amount of blood flowing through an artery in the subject.

17. The MRI system as recited in claim 13 in which each pulse sequence is a gradient recalled echo pulse sequence in which a line in k-space is sampled during the acquisition of an NMR signal by the rf system and the pulse generator repeats the pulse sequence to acquire a plurality of lines in k-space which sample k-space completely to one side of the center of k-space.

18. The MRI system as recited in claim 17 in which the pulse generator repeats the pulse sequence to also acquire a plurality of lines in k-space which partially sample to the other side of the center of k-space.

* * * * *